(12) United States Patent
Boyd

(10) Patent No.: US 11,358,926 B2
(45) Date of Patent: Jun. 14, 2022

(54) COMPOSITIONS FOR PREVENTING AND/OR TREATING DEGENERATIVE DISORDERS OF THE CENTRAL NERVOUS SYSTEM AND/OR LYSOSOMAL STORAGE DISORDERS

(71) Applicant: Amicus Therapeutics, Inc., Cranbury, NJ (US)

(72) Inventor: Robert Boyd, Horsham, PA (US)

(73) Assignee: Amicus Therapeutics, Inc., Philadelphia, PA (US)

( * ) Notice: Subject to any disclaimer, the term of this patent is extended or adjusted under 35 U.S.C. 154(b) by 11 days.

(21) Appl. No.: 16/608,592

(22) PCT Filed: Apr. 25, 2018

(86) PCT No.: PCT/US2018/029275
§ 371 (c)(1),
(2) Date: Oct. 25, 2019

(87) PCT Pub. No.: WO2018/200618
PCT Pub. Date: Nov. 1, 2018

(65) Prior Publication Data
US 2020/0055810 A1 Feb. 20, 2020

Related U.S. Application Data

(60) Provisional application No. 62/489,621, filed on Apr. 25, 2017.

(51) Int. Cl.
*C07C 215/44* (2006.01)
*A61P 25/28* (2006.01)
*C07C 233/06* (2006.01)
*A61K 45/06* (2006.01)

(52) U.S. Cl.
CPC .......... *C07C 215/44* (2013.01); *A61P 25/28* (2018.01); *C07C 233/06* (2013.01); *A61K 45/06* (2013.01); *C07B 2200/07* (2013.01)

(58) Field of Classification Search
CPC ..... A61K 31/133; A61K 31/198; A61P 25/28; A61P 25/16
USPC ........................................................ 514/630
See application file for complete search history.

(56) References Cited

U.S. PATENT DOCUMENTS

2008/0255239 A1   10/2008   Chow et al.
2015/0258081 A1*   9/2015   Lukas ..................... A61P 43/00
                                                                   514/315

FOREIGN PATENT DOCUMENTS

| JP | 2003155229 A |   | 5/2003 |
| JP | 2012158523   | * | 8/2012 |
| JP | 2013508366 A |   | 3/2013 |
| JP | 2013508367 A |   | 3/2013 |
| WO | 2011049736 A1 |  | 4/2011 |
| WO | 2011049737 A1 |  | 4/2011 |

OTHER PUBLICATIONS

Tongco et al. Synlett 1997, 1193.*
Ogawa et al. Mini-Reviews in Medicinal Chemistry year 2007, 7(7),679-691.*
Thornber, Chem. Soc. Rev.,year 1979, 563-580.*
CAS Registry STN Substance Record for RN1393687-66-5 , Sep. 6, 2012.*
Wermuth, C. G., "The Latest Medicinal Chemistry", vol. 1, 1998, pp. 375-380.

* cited by examiner

*Primary Examiner* — Ana Z Muresan
(74) *Attorney, Agent, or Firm* — Servilla Whitney LLC

(57) ABSTRACT

The present invention provides novel compounds as well as compositions and methods using the same for preventing and/or treating degenerative disorders of the central nervous system and/or lysosomal storage disorders. In particular, the present invention provides methods for preventing and/or treating Parkinson's disease, Alzheimer's disease and/or Gaucher's disease.

5 Claims, No Drawings

COMPOSITIONS FOR PREVENTING AND/OR TREATING DEGENERATIVE DISORDERS OF THE CENTRAL NERVOUS SYSTEM AND/OR LYSOSOMAL STORAGE DISORDERS

CROSS-REFERENCE TO RELATED APPLICATIONS

This application is the National Stage entry of PCT/US18/29275, filed on Apr. 25, 2018, which claims priority to U.S. Application No. 62/489,621, filed on Apr. 25, 2017, both of which are incorporated herein by reference in their entireties.

FIELD OF THE INVENTION

The present invention provides novel compounds, known as pharmacological chaperones, as well as compositions and methods using the same for preventing and/or treating degenerative disorders of the central nervous system and/or lysosomal storage disorders. In particular, the present invention provides methods for preventing and/or treating Parkinson's disease, Alzheimer's disease and/or Gaucher's disease.

BACKGROUND OF THE INVENTION

Many degenerative disorders of the central nervous system are associated with pathologic aggregation of proteins or lipids. For example, synucleinopathies are a group of diseases that arise from disruption of synuclein protein homeostasis. In particular, alpha-synuclein aggregation is associated with pathological conditions characterized by Lewy bodies, such as Parkinson's disease, dementia with Lewy bodies, and multiple system atrophy. Likewise, alpha-synuclein fragment, non-Abeta component, is found in amyloid plaques of Alzheimer's disease. Recently, enhancement of glucocerebrosidase (beta-glucosidase; GCase) activity in the brain has been shown to prevent accumulation of synuclein in the brain (Sean Clark, Ying Sun, You-Hal Xu, Gregory Grabowski, and Brandon Wustman, "A biochemical link between Gaucher's and Parkinson's disease and a potential new approach to treating synucleinopathies: a pharmacological chaperone for beta-glucocerebrosidase prevents accumulation of alpha-synuclein in a Parkinson's mouse model," Presented at the Society for Neuroscience Annual Meeting, San Diego, Calif., 2007). Thus, agents that enhance GCase activity may provide relief for patients at risk for developing or diagnosed with degenerative disorders of the central nervous system.

Lysosomal storage disorders are caused by a defect in lysosomal function that results in accumulation of substances within the lysosome of cells. This defect is usually a consequence of deficiency of a single enzyme required for the metabolism of lipid, glycogen, glycoprotein, or mucopolysaccharide. Gaucher's disease, the most common lysosomal storage disorder, is characterized by accumulation of the glycolipid glucocerebroside (also known as glucosylceramide). Symptoms of Gaucher's disease include enlarged spleen and liver, liver malfunction, skeletal disorders and bone lesions that may be painful, severe neurologic complications, swelling of lymph nodes and (occasionally) adjacent joints, distended abdomen, a brownish tint to the skin, anemia, low blood platelets and yellow fatty deposits on the sclera. In addition, persons affected with Gaucher's disease may also be more susceptible to infection.

There is a need for new therapeutic compounds that can be used to prevent and/or treat degenerative disorders of the central nervous system and/or lysosomal storage disorders, which will provide patients with a higher quality of life and achieve a better clinical outcome. In particular, there is a need for new therapeutic compounds to prevent and/or treat synucleinopathies, such as Parkinson's disease and Alzheimer's disease, and lysosomal storage disorders such as Gaucher's disease, which will provide patients with a higher quality of life and achieve a better clinical outcome.

SUMMARY OF THE INVENTION

The present invention provides novel compounds as well as compositions and methods using the same to prevent and/or treat a degenerative disorder of the central nervous system and/or a lysosomal storage disorder in a patient at risk for developing or diagnosed with the same, which includes administering to the patient in need thereof an effective amount of a compound described herein.

In one aspect, there is provided a compound as well as compositions and methods using the same to prevent and/or treat a degenerative disorder of the central nervous system and/or a lysosomal storage disorder in a patient at risk for developing or diagnosed with the same, which includes administering to the patient in need thereof an effective amount of a compound defined by Formula I:

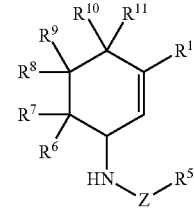

wherein:
$R^1$ is $C(R^2)(R^3)(R^4)$;
$R^2$ is hydrogen, —OH or halogen;
$R^3$ is hydrogen, —OH, halogen or $C_{1-8}$ alkyl;
$R^4$ is hydrogen, —OH, halogen, $C_{1-8}$ alkyl, substituted $C_{1-8}$ alkyl, aryl, substituted aryl, alkylcycloalkyl or substituted alkylcycloalkyl;
$R^3$ and $R^4$ may join with the carbon to which they are attached to form a cycloalkyl ring, which may be optionally substituted, preferably with halogen and more preferably with one or more fluorine atoms;
Z is optional, when present Z is —$(CH_2)_{1-8}$—, —C(=O)—, —S(=O)$_2$NH—, —S(=O)$_2$—, —C(=S)NH—, —S(=O)$_2$—$CH_3$, C(=O)—NH—, —S(=O)$_2$—$NR^{12}R^{13}$, —C(=O)$C_{1-8}$ alkyl or —C(=O)CH(NH$_2$)CH$_3$;
$R^{12}$ is hydrogen, $C_{1-8}$ alkyl or substituted $C_{1-8}$ alkyl;
$R^{13}$ is hydrogen, $C_{1-8}$ alkyl or substituted $C_{1-8}$ alkyl;
$R^5$ is hydrogen, $C_{1-8}$ alkyl, substituted $C_{1-8}$ alkyl, aryl, substituted aryl, $C_{1-8}$ alkenyl, substituted $C_{1-8}$ alkenyl, arylalkyl, substituted arylalkyl, alkylaryl, substituted alkylaryl, aminoarylalkyl or substituted aminoarylalkyl;
$R^6$ is hydrogen, halogen, $C_{1-8}$ alkyl, substituted $C_{1-8}$ alkyl, arylalkyl, substituted arylalkyl, alkylaryl, or substituted alkylaryl;
$R^7$ is hydrogen, —OH or halogen;

$R^8$ is hydrogen, halogen, $C_{1-8}$ alkyl, substituted $C_{1-8}$ alkyl, arylalkyl, substituted arylalkyl, alkylaryl, or substituted alkylaryl;

$R^9$ is hydrogen, —OH or halogen;

$R^{10}$ is hydrogen, halogen, $C_{1-8}$ alkyl, substituted $C_{1-8}$ alkyl, arylalkyl, substituted arylalkyl, alkylaryl, or substituted alkylaryl; and $R^{11}$ is hydrogen, —OH or halogen, provided that at least one of $R^2$, $R^3$, $R^4$, $R^6$, $R^7$, $R^8$, $R^9$, $R^{10}$ or $R^{11}$ comprises a halogen.

In another aspect, there is provided a compound as well as compositions and methods using the same to prevent and/or treat a degenerative disorder of the central nervous system and/or a lysosomal storage disorder in a patient at risk for developing or diagnosed with the same, which includes administering to the patient in need thereof an effective amount of a compound defined by Formula II:

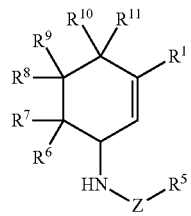

wherein:

$R^1$ is $C(R^2)(R^3)(R^4)$;

$R^2$ is hydrogen, —OH or halogen;

$R^3$ is hydrogen, —OH, halogen or —CH$_3$;

$R^4$ is hydrogen, halogen, —CH$_3$, phenyl, fluorophenyl, methylphenyl or cyclohexylmethyl;

$R^3$ and $R^4$ may join with the carbon to which they are attached to form a cycloalkyl ring, which may be optionally substituted with one or more halogen atoms;

Z is optional, when present Z is —(CH$_2$)—, —C(=O)—, —S(=O)$_2$NH—, —S(=O)$_2$—, —S(=O)$_2$—CH$_3$, C(=O)—NH—, —S(=O)$_2$NR$^{12}$R$^{13}$, —C(=S)—NH— or —C(=O)$_2$—CH$_3$, $R^{12}$ is hydrogen or CH$_3$;

$R^{13}$ is hydrogen or CH$_3$;

$R^5$ is hydrogen or aminophenylalkyl;

$R^6$ is hydrogen, halogen or —CH$_3$;

$R^7$ is hydrogen, —OH or halogen;

$R^8$ is hydrogen, halogen or —CH$_3$;

$R^9$ is hydrogen, —OH or halogen;

$R^{10}$ is hydrogen, halogen or —CH$_3$; and $R^{11}$ is hydrogen, —OH or halogen;

provided that at least one of $R^2$, $R^3$, $R^4$, $R^6$, $R^7$, $R^8$, $R^9$, $R^{10}$ or $R^{11}$ comprises a halogen.

In yet another aspect, there is provided a compound as well as compositions and methods using the same to prevent and/or treat a degenerative disorder of the central nervous system and/or a lysosomal storage disorder in a patient at risk for developing or diagnosed with the same, which includes administering to the patient in need thereof an effective amount of a compound defined by Formula III:

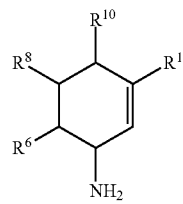

wherein:

$R^1$ is $C(R^2)(R^3)(R^4)$;

$R^2$ is hydrogen, —OH or halogen;

$R^3$ is hydrogen, —OH, halogen or —CH$_3$;

$R^4$ is hydrogen, halogen, —CH$_3$, phenyl, fluorophenyl, methylphenyl or cyclohexylmethyl;

$R^3$ and $R^4$ may join with the carbon to which they are attached to form a cycloalkyl ring, which may be optionally substituted with one or more halogen atoms;

$R^6$ is —OH or halogen;

$R^8$ is —OH or halogen; and $R^{10}$ is —OH or halogen;

provided that that at least one of $R^2$, $R^3$, $R^4$, $R^6$, $R^8$ or $R^{10}$ comprises a halogen.

It is understood by a person of ordinary skill in the art that $R^2$, $R^3$ and $R^4$ in aforementioned Formulas I, II, and III will not be selected such that an unstable molecule will result.

In still another aspect, there is provided a compound as well as compositions and methods using the same to prevent and/or treat a degenerative disorder of the central nervous system and/or a lysosomal storage disorder in a patient at risk for developing or diagnosed with the same, which includes administering to the patient in need thereof an effective amount of a compound selected from the following:

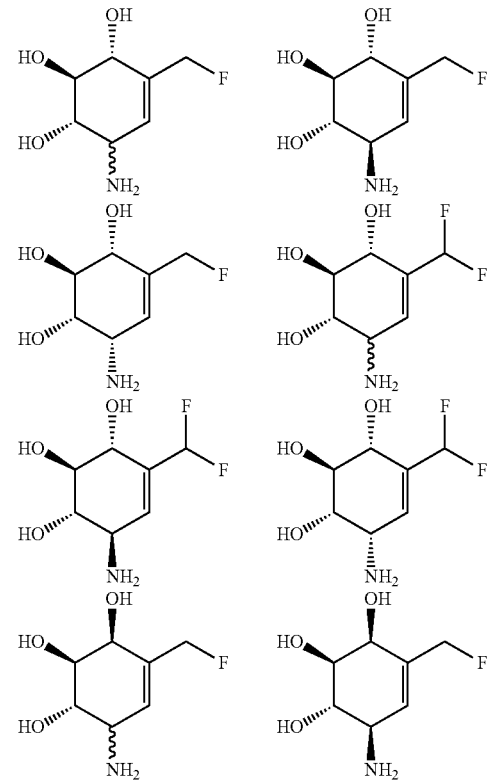

-continued

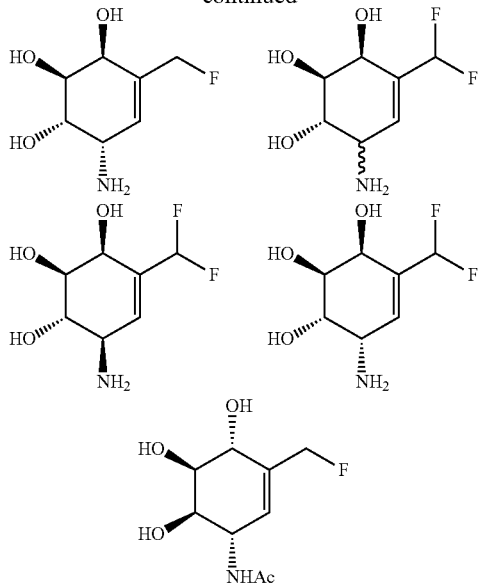

or a pharmaceutically acceptable salt, solvate, or prodrug thereof.

In one embodiment, the compound is (1S,2S,3R,6S)-6-amino-4-(fluoromethyl)cyclohex-4-ene-1,2,3-triol, (1S,2S,3R,6R)-6-amino-4-(fluoromethyl)cyclohex-4-ene-1,2,3-triol, (1S,2S,3S,6S)-6-amino-4-(fluoromethyl)cyclohex-4-ene-1,2,3-triol, (1S,2S,3S,6R)-6-amino-4-(fluoromethyl)cyclohex-4-ene-1,2,3-triol or a pharmaceutically acceptable salt, solvate, or prodrug thereof. In one embodiment, the compound is (1S,2S,3R,6S)-6-amino-4-(fluoromethyl)cyclohex-4-ene-1,2,3-triol, or a pharmaceutically acceptable salt, solvate, or prodrug thereof. In one embodiment, the compound is (1S,2S,3R,6R)-6-amino-4-(fluoromethyl)cyclohex-4-ene-1,2,3-triol, or a pharmaceutically acceptable salt, solvate, or prodrug thereof. In one embodiment, the compound is ((1S,2S,3S,6S)-6-amino-4-(fluoromethyl)cyclohex-4-ene-1,2,3-triol, or a pharmaceutically acceptable salt, solvate, or prodrug thereof. In one embodiment, the compound is ((1S,2S,3S,6R)-6-amino-4-(fluoromethyl)cyclohex-4-ene-1,2,3-triol, or a pharmaceutically acceptable salt, solvate, or prodrug thereof.

In one embodiment, the compound is (1S,2S,3R,6S)-6-amino-4-(difluoromethyl)cyclohex-4-ene-1,2,3-triol, (1S,2S,3R,6R)-6-amino-4-(difluoromethyl)cyclohex-4-ene-1,2,3-triol, (1S,2S,3S,6S)-6-amino-4-(difluoromethyl)cyclohex-4-ene-1,2,3-triol, (1S,2S,3S,6R)-6-amino-4-(difluoromethyl)cyclohex-4-ene-1,2,3-triol or a pharmaceutically acceptable salt, solvate, or prodrug thereof. In one embodiment, the compound is (1S,2S,3R,6S)-6-amino-4-(difluoromethyl)cyclohex-4-ene-1,2,3-triol, or a pharmaceutically acceptable salt, solvate, or prodrug thereof. In one embodiment, the compound is (1S,2S,3R,6R)-6-amino-4-(difluoromethyl)cyclohex-4-ene-1,2,3-triol, or a pharmaceutically acceptable salt, solvate, or prodrug thereof. In one embodiment, the compound is ((1S,2S,3S,6S)-6-amino-4-(difluoromethyl)cyclohex-4-ene-1,2,3-triol, or a pharmaceutically acceptable salt, solvate, or prodrug thereof. In one embodiment, the compound is ((1S,2S,3S,6R)-6-amino-4-(difluoromethyl)cyclohex-4-ene-1,2,3-triol, or a pharmaceutically acceptable salt, solvate, or prodrug thereof.

In one embodiment, the compound is N-((1S,4R,5S,6R)-3-(fluoromethyl)-4,5,6-trihydroxycyclohex-2-en-1-yl)acetamide or a pharmaceutically acceptable salt, solvate, or prodrug thereof.

In one embodiment, the degenerative disorder is a synucleinopathy. In one embodiment, the degenerative disorder is characterized by Lewy bodies. In one embodiment, the degenerative disorder is Parkinson's disease, dementia with Lewy bodies, multiple system atrophy or Alzheimer's disease. In one embodiment, the degenerative disorder is associated with aggregation of at least one protein. In one embodiment, the degenerative disorder is associated with aggregation of alpha-synuclein. In one embodiment, the degenerative disorder is associated with aggregation of non-Abeta component. In one embodiment, the degenerative disorder is associated with accumulation of at least one glycolipid. In one embodiment, the degenerative disorder is associated with accumulation of at least one glycosphingolipid. In one embodiment, the degenerative disorder is associated with accumulation of glucocerebroside. In one embodiment, the degenerative disorder is associated with a mutation in glucocerebrosidase.

The present invention also provides methods for preventing and/or treating a degenerative disorder of the central nervous system in a patient at risk for developing or diagnosed with the same, which comprises administering to the patient in need thereof an effective amount of any of the aforementioned compounds, or a pharmaceutically acceptable salt, solvate, or prodrug thereof, or any combination of two or more thereof.

In one embodiment, the degenerative disorder of the central nervous system is an α-synucleinopathy. In one embodiment, the degenerative disorder of the central nervous system is Parkinson's disease. In one embodiment, the degenerative disorder of the central nervous system is Alzheimer's disease.

In one embodiment, the method of preventing and/or treating the degenerative disorder of the central nervous system further comprises administering an effective amount of at least one other therapeutic agent. In one embodiment, at least one other therapeutic agent is levodopa, an anticholinergic, a catechol-O-methyl transferase inhibitor, a dopamine receptor agonist, a monoamine oxidase inhibitor, a peripheral decarboxylase inhibitor, or an anti-inflammatory agent.

In one embodiment, the lysosomal storage disorder is associated with accumulation of at least one glycolipid. In one embodiment, the lysosomal storage disorder is associated with accumulation of at least one glycosphingolipid. In one embodiment, the lysosomal storage disorder is associated with accumulation of glucocerebroside. In one embodiment, the lysosomal storage disorder is associated with a deficiency in glucocerebrosidase. In one embodiment, the lysosomal storage disorder is associated with a mutation in glucocerebrosidase. In one embodiment, the lysosomal storage disease is Niemann-Pick disease. In one embodiment, the lysosomal storage disease is Gaucher's disease.

The present invention also provides methods for preventing and/or treating a lysosomal storage disorder in a patient at risk for developing or diagnosed with the same, which comprises administering to the patient in need thereof an effective amount of a composition comprising a compound of Formula I, or a pharmaceutically acceptable salt, solvate, or prodrug thereof.

In one embodiment, the lysosomal storage disorder is Gaucher's disease.

In one embodiment, the method of preventing and/or treating a lysosomal storage disorder further comprises administering an effective amount of at least one other therapeutic agent. In one embodiment, at least one other therapeutic agent is imiglucerase or 1,5-(butylimino)-1,5-dideoxy-D-glucitol.

The present invention also provides kits comprising:
a container having an effective amount of any of the compounds of the present invention, alone or in combination; and
instructions for using the same to prevent or treat a degenerative disorder of the central nervous system or a lysosomal storage disorder.

DETAILED DESCRIPTION OF THE INVENTION

As used herein the following terms shall have the definitions set forth below.

As used herein, the phrase "degenerative disorder of the central nervous system" means any disorder associated with the premature degeneration of any component of the central nervous system, such as neurons, myelin sheaths or axons. Such disorders include but are not limited to multi-infarct dementia, Huntington's disease, Pick's disease, amyotrophic lateral sclerosis, Creutzfeldt-Jakob's disease, frontal-lobe degeneration, corticobasal degeneration, progressive supranuclear palsy, Parkinson's disease, dementia with Lewy bodies, multiple system atrophy or Alzheimer's disease.

As used herein the phrase "lysosomal storage disorder" refers to any of a group of diseases resulting from abnormal metabolism resulting in accumulation of a substrate in the lysosome. Table 1 contains a non-limiting list of exemplary lysosomal storage disorders and their associated defective enzyme.

TABLE 1

Lysosomal storage disorders

| Lysosomal storage disorder | Defective enzyme |
|---|---|
| Pompe disease | Acid α-glucosidase |
| Gaucher disease | Acid β-glucosidase or glucocerebrosidase |
| Fabry disease | α-Galactosidase A |
| $G_{M1}$-gangliosidosis | Acid β-galactosidase |
| Tay-Sachs disease | β-Hexosaminidase A |
| Sandhoff disease | β-Hexosaminidase B |
| Niemann-Pick disease | Acid sphingomyelinase |
| Krabbe disease | Galactocerebrosidase |
| Farber disease | Acid ceramidase |
| Metachromatic leukodystrophy | Arylsulfatase A |
| Hurler-Scheie disease | α-L-Iduronidase |
| Hunter disease | Iduronate-2-sulfatase |
| Sanfilippo disease A | Heparan N-sulfatase |
| Sanfilippo disease B | α-N-Acetylglucosaminidase |
| Sanfilippo disease C | Acetyl-CoA: α-glucosaminide N-acetyltransferase |
| Sanfilippo disease D | N-Acetylglucosamine-6-sulfate sulfatase |
| Morquio disease A | N-Acetylgalactosamine-6-sulfate sulfatase |
| Morquio disease B | Acid β-galactosidase |
| Maroteaux-Lamy disease | Arylsulfatase B |
| Sly disease | β-Glucuronidase |
| alpha.-Mannosidosis | Acid α-mannosidase |
| beta,-Mannosidosis Acid | β-mannosidase |
| Fucosidosis | Acid α-L-fucosidase |
| Sialidosis | Sialidase |
| Schindler-Kanzaki disease | α-N-acetylgalactosaminidase |

As used herein the term "treating" means to ameliorate one or more symptoms associated with the referenced disorder.

As used herein, the term "preventing" means to mitigate a symptom of the referenced disorder.

As used herein the phrase "an effective amount" means an amount effective to prevent and/or treat a patient at risk for developing or diagnosed with the referenced disorder, and thus producing the desired therapeutic effect.

As used herein the term "patient" means a mammal (e.g., a human).

Listed below are chemical definitions of various terms used to describe this invention. These definitions apply to the terms as they are used throughout this specification, unless otherwise limited in specific instances, either individually or as part of a larger group.

The term "alkyl" refers to straight or branched chain unsubstituted hydrocarbon groups of 1 to 20 carbon atoms, preferably 1 to 8 carbon atoms, more preferably 1 to 6 carbon atoms. The expression "lower alkyl" refers to unsubstituted alkyl groups of 1 to 4 carbon atoms.

The term "substituted alkyl" refers to an alkyl group substituted by, for example, one to four substituents, such as, halo, hydroxy, alkoxy, oxo, alkanoyl, aryloxy, alkanoyloxy, amino, alkylamino, arylamino, aralkylamino, disubstituted amines in which the 2 amino substituents are selected from alkyl, aryl or aralkyl; alkanoylamino, aroylamino, aralkanoylamino, substituted alkanoylamino, substituted arylamino, substituted aralkanoylamino, thiol, alkylthio, arylthio, aralkylthio, alkylthiono, arylthiono, aralkylthiono, alkylsulfonyl, arylsulfonyl, aralkylsulphonyl, sulfonamido, e.g. $SO_2NH_2$, substituted sulfonamido, nitro, cyano, carboxy, carbamyl, e.g. $CONH_2$, substituted carbamyl e.g. CONHalkyl, CONHaryl, CONHaralkyl or cases where there are two substituents on the nitrogen selected from alkyl, aryl or aralkyl; alkoxycarbonyl, aryl, substituted aryl, guanidino and heterocyclos, such as, indolyl, imidazolyl, furyl, thienyl, thiazolyl, pyrrolidyl, pyridyl, pyrimidyl and the like. Where noted above where the substituent is further substituted it will be with alkyl, alkoxy, aryl or aralkyl.

The term "halogen" or "halo" refers to fluorine, chlorine, bromine and iodine.

The term "aryl" refers to monocyclic or bicyclic aromatic hydrocarbon groups having 6 to 12 carbon atoms in the ring portion, such as phenyl, naphthyl, biphenyl and diphenyl groups, each of which may be substituted.

The term "aralkyl" refers to an aryl group bonded directly through an alkyl group, such as benzyl. Similarly, the term "alkylaryl" refers to an alkyl group bonded directly through an aryl group, such as methylbenzyl.

The term "substituted aryl" refers to an aryl group substituted by, for example, one to four substituents such as alkyl, substituted alkyl, halo, trifluoromethoxy, trifluoromethyl, hydroxy, alkoxy, alkanoyl, alkanoyloxy, amino, alkylamino, aralkylamino, dialkylamino, alkanoylamino, thiol, alkylthio, ureido, nitro, cyano, carboxy, carboxyalkyl, carbamyl, alkoxycarbonyl, alkylthiono, arylthiono, arylsulfonylamine, sulfonic acid, alkysulfonyl, sulfonamido, aryloxy and the like. The substituent may be further substituted by hydroxy, alkyl, alkoxy, aryl, substituted aryl, substituted alkyl or aralkyl.

The term "heteroaryl" refers to an optionally substituted, aromatic group for example, which is a 4 to 7 membered monocyclic, 7 to 11 membered bicyclic, or 10 to 15 membered tricyclic ring system, which has at least one heteroatom and at least one carbon atom-containing ring, for example, pyridine, tetrazole, indazole.

The term "alkenyl" refers to straight or branched chain hydrocarbon groups of 2 to 20 carbon atoms, preferably 2 to 15 carbon atoms, and most preferably 2 to 8 carbon atoms, having one to four double bonds.

The term "substituted alkenyl" refers to an alkenyl group substituted by, for example, one to two substituents, such as, halo, hydroxy, alkoxy, alkanoyl, alkanoyloxy, amino, alkylamino, dialkylamino, alkanoylamino, thiol, alkylthio, alkylthiono, alkylsulfonyl, sulfonamido, nitro, cyano, carboxy, carbamyl, substituted carbamyl, guanidino, indolyl, imidazolyl, furyl, thienyl, thiazolyl, pyrrolidyl, pyridyl, pyrimidyl and the like.

The term "alkynyl" refers to straight or branched chain hydrocarbon groups of 2 to 20 carbon atoms, preferably 2 to 15 carbon atoms, and most preferably 2 to 8 carbon atoms, having one to four triple bonds.

The term "substituted alkynyl" refers to an alkynyl group substituted by, for example, a substituent, such as, halo, hydroxy, alkoxy, alkanoyl, alkanoyloxy, amino, alkylamino, dialkylamino, alkanoylamino, thiol, alkylthio, alkylthiono, alkylsulfonyl, sulfonamido, nitro, cyano, carboxy, carbamyl, substituted carbamyl, guanidino and heterocyclo, e.g. imidazolyl, furyl, thienyl, thiazolyl, pyrrolidyl, pyridyl, pyrimidyl and the like.

The term "cycloalkyl" refers to an optionally substituted, saturated cyclic hydrocarbon ring systems, preferably containing 1 to 3 rings and 3 to 7 carbons per ring which may be further fused with an unsaturated C3-C7 carbocylic ring. Exemplary groups Include cyclopropyl, cyclobutyl, cyclopentyl, cyclohexyl, cycloheptyl, cycloctyl, cyclodecyl, cyclododecyl, and adamantyl. Exemplary substituents include one or more alkyl groups as described above, or one or more groups described above as alkyl substituents.

The terms "heterocycle", "heterocyclic" and "heterocyclo" refer to an optionally substituted, fully saturated or unsaturated, aromatic or nonaromatic cyclic group, for example, which is a 4 to 7 membered monocyclic, 7 to 11 membered bicyclic, or 10 to 15 membered tricyclic ring system, which has at least one heteroatom in at least one carbon atom-containing ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized and the nitrogen heteroatoms may also optionally be quaternized. The heterocyclic group may be attached at any heteroatom or carbon atom.

Exemplary monocyclic heterocyclic groups include pyrrolidinyl, pyrrolyl, indolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxazepinyl, azepinyl, 4-piperidonyl, pyridyl, N-oxopyridyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1, 1-dioxothienyl, dioxanyl, isothiazolidinyl, thietanyl, thiiranyl, triazinyl, and triazolyl, and the like.

Exemplary bicyclic hetrocyclic groups include 2,3-dihydro-2-oxo-1H-indolyl, benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl (such as furo[2,3-c]pyridinyl, furo[3,1-b]pyridinyl or furo[2,3-b]pyridinyl), dihydroisoindolyl, dihydroquinazolinyl (such as 3,4-dihydro-4-oxo-quinazolinyl), benzisothiazolyl, benzisoxazolyl, benzodiazinyl, benzofurazanyl, benzothiopyranyl, benzotriazolyl, benzpyrazolyl, dihydrobenzofuryl, dihydrobenzothienyl, dihydrobenzothiopyranyl, dihydrobenzothiopyranyl sulfone, dihydrobenzopyranyl, indolinyl, isochromanyl, isoindolinyl, naphthyridinyl, phthalazinyl, piperonyl, purinyl, pyridopyridyl, quinazolinyl, tetrahydroquinolinyl, thienofuryl, thienopyridyl, thienothienyl, and the like.

Exemplary substituents include one or more alkyl or aralkyl groups as described above or one or more groups described above as alkyl substituents.

Also included are smaller heterocyclos, such as, epoxides and aziridines.

The term "heteroatoms" shall include oxygen, sulfur and nitrogen.

Degenerative Disorders of the Central Nervous System

Parkinson's disease may be diagnosed in patients according to the United Kingdom Parkinson's Disease Society brain-bank clinical diagnostic criteria (see, Hughes et al., Accuracy of clinical diagnosis of idiopathic Parkinson's disease: a clinico-pathological study of 100 cases. J Neurol Neurosurg Psychiatry 1992; 55:181-184) and/or the criteria described by Gelb et al., Diagnostic Criteria for Parkinson's Disease. *Arch Neurol.* 1999; 56(1):33-39. Likewise, the severity of Parkinson's disease may be ascertained using the Unified Parkinson's Disease Rating Scale. See, e.g., Fahn and Elton, Members of the Unified Parkinson's Disease Rating Scale Development Committee. Unified Parkinson's Disease Rating Scale. In: Fahn et al., Recent developments in Parkinson's disease. New York: Macmillan, 1987: 153-183.

Alzheimer's disease may be diagnosed in patients according to the criteria for dementia of the Alzheimer's type of the Diagnostic and Statistical Manual of Mental Disorders, 4$^{th}$ ed.: DSM-IV. Washington, D.C.: American Psychiatric Association, 1994. Likewise, the criteria for probable Alzheimer's disease may be ascertained based on criteria of the National Institute of Neurological and Communicative Disorders and Stroke and the Alzheimer's Disease and Related Disorders Association. See also, McKhann et al., Clinical diagnosis of Alzheimer's disease: report of the NINCDS-ADRDA work group under the auspices of Department of Health and Human Services Task Force on Alzheimer's Disease. Neurology 1984; 34:939-944.

Multiple system atrophy (MSA) is characterized by glial cytoplasmic inclusion bodies (also known as Papp-Lantos bodies) in the movement, balance and automatic control centers of the brain. The most common first sign of MSA is the appearance of an "akinetic-rigid syndrome" (i.e., slowness of initiation of movement resembling Parkinson's disease) found in 62% at first presentation. Other common signs at onset include problems with balance (found in 22%), followed by genito-urinary problems (9%). For men, the first sign can be erectile dysfunction (unable to achieve or sustain an erection). Both men and women often experience problems with their bladders including urgency, frequency, incomplete bladder emptying or an inability to pass urine (retention). About 1 in 5 MSA patients will suffer a fall in their first year of disease. As the disease progresses three groups of symptoms predominate. These are: (i) parkinsonism (slow, stiff movement, writing becomes small and spidery); (ii) cerebellar dysfunction (difficulty coordinating movement and balance); and (iii) autonomic dysfunction (impaired automatic body functions) including: postural or orthostatic hypotension, resulting in dizziness or fainting upon standing up, urinary incontinence, impotence; constipation; dry mouth and skin; trouble regulating body temperature due to abnormal sweating; abnormal breathing during sleep. Notably, not all of these symptoms are experienced by all patients.

Dementia with Lewy bodies (DLB) is one of the most common types of progressive dementia. The central feature of DLB is progressive cognitive decline, combined with three additional defining features: (1) pronounced "fluctuations" in alertness and attention, such as frequent drowsiness, lethargy, lengthy periods of time spent staring into space, or disorganized speech; (2) recurrent visual hallucinations, and (3) parkinsonian motor symptoms, such as rigidity and the loss of spontaneous movement. People may also suffer from depression. The symptoms of DLB are caused by the build-up of Lewy bodies—accumulated bits of alpha-synuclein protein—inside the nuclei of neurons in areas of the brain that control particular aspects of memory and motor control. Researchers don't know exactly why alpha-synuclein accumulates into Lewy bodies or how Lewy bodies cause the symptoms of DLB, but they do know that alpha-synuclein accumulation is also linked to Parkinson's disease, multiple system atrophy, and several other disorders, which are referred to as the "synucleinopathies." The similarity of symptoms between DLB and Parkinson's disease, and between DLB and Alzheimer's disease, can often make it difficult for a doctor to make a definitive diagnosis. In addition, Lewy bodies are often also found in the brains of people with Parkinson's and Alzheimer's diseases. These findings suggest that either DLB is related to these other causes of dementia or that an individual can have both diseases at the same time. DLB usually occurs sporadically, in people with no known family history of the disease. However, rare familial cases have occasionally been reported.

Lysosomal Storage Disorders

The most common lysosomal storage disorder, Gaucher's disease, is characterized by accumulation of the glycolipid glucocerebroside (also known as glucosylceramide). Three phenotypes have been described for Gaucher's disease that are denoted by the absence (type 1) or presence of neurologic involvement during childhood (type 2) or adolescence (type 3). For example, see Grabowski, Gaucher's disease. Adv Hum Genet 1993; 21:377-441.

The three types of Gaucher's disease are inherited in an autosomal recessive fashion. Both parents must be carriers in order for a child to be affected. If both parents are carriers, there is a one in four, or 25%, chance with each pregnancy for an affected child. Genetic counseling and genetic testing is recommended for families who may be carriers of mutations. Each type has been linked to particular mutations. In all, there are about 80 known mutations that lead to Gaucher's disease (see, e.g., McKusick, V. A.: Mendelian Inheritance in Man. A Catalog of Human Genes and Genetic Disorders. Baltimore: Johns Hopkins University Press, 1998 (12th edition)).

Type 1 Gaucher's disease is panethnic, but is especially prevalent among persons of Ashkenazi Jewish descent, with a carrier rate of 1 in 17 Ashkenazi Jews. The N370S and 84GG mutations are the most frequent mutations in the glucocerebrosidase gene among Ashkenazi Jews, with rates of 1 in 17.5 for N370S and 1 in 400 for 84GG in the general healthy Ashkenazi population, and are associated with mild and severe Gaucher's disease, respectively. The 84GG mutation occurs almost exclusively among Ashkenazi Jews. Other rare glucocerebrosidase gene variants identified in patients of Ashkenazi descent with Gaucher's disease include L444P, IVS2+1G→A, V394L, and R496H. In contrast to presentation of Type 1 Gaucher's disease in Ashkenazi Jews, Type 1 Gaucher's disease tends to be severe and progressive in Japanese patients (see, Ida et al., Type 1 Gaucher Disease Patients: Phenotypic Expression and Natural History in Japanese Patients, Blood Cells, Molecules and Diseases, 1984, 24(5):73-81). In addition, Type 3 Gaucher's disease, associated with one or two copies of glucocerebrosidase gene variant L444P is prevalent in Swedish patients from the Norrbotten region.

A definitive diagnosis of Gaucher's disease is made with genetic testing. As there are numerous different mutations, sequencing of the glucocerebrosidase gene is sometimes necessary to confirm the diagnosis. Prenatal diagnosis is available, and is useful when there is a known genetic risk factor. However, a diagnosis of Gaucher's disease can also be implied by biochemical abnormalities such as high alkaline phosphatase, angiotensin-converting enzyme (ACE) and immunoglobulin levels, or by cell analysis showing "crinkled paper" cytoplasm and glycolipid-laden macrophages. Notably, Niemann-Pick disease is similar in that it is characterized by accumulation of $G_{M2}$-gangliosides and $G_{M1}$-gangliosides in addition to glucocerebroside (Vanier et al., *Brain Pathology.* 1998; 8: 163-74).

Symptoms of Gaucher's disease include the following:
Painless hepatomegaly and splenomegaly (the size of the spleen can be 1500-3000 ml, as opposed to the normal size of 50-200 ml)
Hypersplenism: the rapid and premature destruction of blood cells, leading to anemia, neutropenia and thrombocytopenia (with an increased risk of infection and bleeding)
Cirrhosis of the liver, though rare
Neurological symptoms occur only in some types of Gaucher's (see below):
  Type II: serious convulsions, hypertonia, mental retardation, apnea.
  Type III: muscle twitches known as myoclonus, convulsions, dementia, ocular muscle apraxia.
Osteoporosis: 75% develop visible bony abnormalities due to the accumulated glucosylceramide. A deformity of the distal femur in the shape of an Erlenmeyer flask is commonly described.
Yellowish-brown skin pigmentation Compounds Novel compounds of the present invention are provided below:

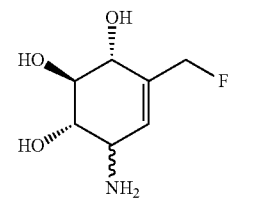

(1S,2S,3R)-6-amino-4 (fluoromethyl)cyclohexene-1,2,3-triol

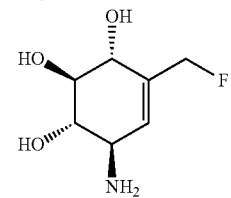

(1S,2S,3R,6R)-6-amino-4 (fluoromethyl)cyclohexene-1,2,3-triol

-continued

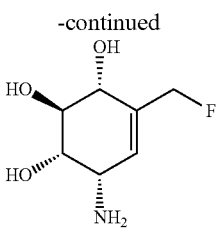

(1S,2S,3R,6S)-6-amino-4
(fluoromethyl)cyclohexene-1,2,3-triol

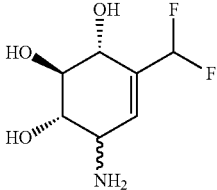

(1S,2S,3R)-6-amino-4-(difluoromethyl)
cyclohexene-1,2,3-triol

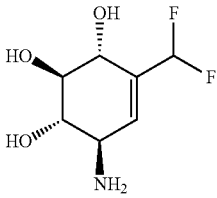

(1S,2S,3R,6R)-6-amino-4-
(difluoromethyl)cyclohexene-1,2,3-triol

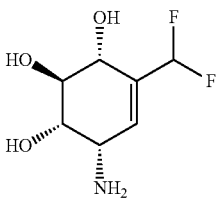

(1S,2S,3R,6S)-6-amino-4-
(difluoromethyl)cyclohexene-1,2,3-triol

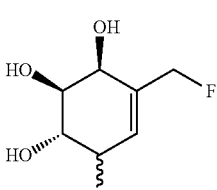

(1S,2S,3S)-6-amino-4 (fluoromethyl)
cyclohexene-1,2,3-triol

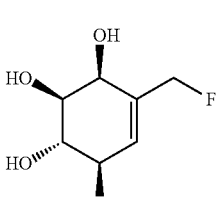

(1S,2S,3S,6R)-6-amino-4
(fluoromethyl)cyclohexene-1,2,3-triol

-continued

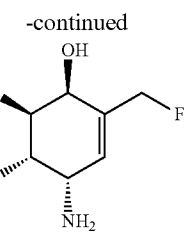

(1S,2S,3S,6S)-6-amino-4
(fluoromethyl)cyclohexene-1,2,3-triol

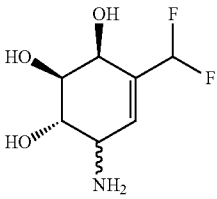

(1S,2S,3S)-6-amino-4-(difluoromethyl)
cyclohexene-1,2,3-triol

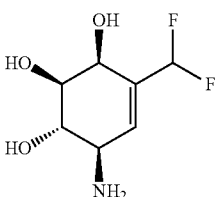

(1S,2S,3S,6R)-6-amino-4-
(difluoromethyl)cyclohexene-1,2,3-triol

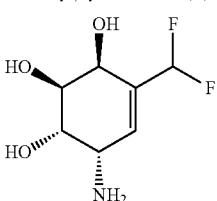

(1S,2S,3S,6S)-6-amino-4-
(difluoromethyl)cyclohexene-1,2,3-triol

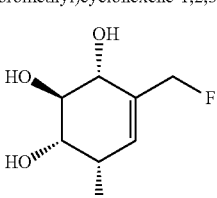

N-((1S,4R,5S,6R)-3-(fluoromethyl)-4,5,6-
trihydroxycyclohex-2-en-1-yl)acetamide

Chemical Process

Synthesis of the valienamine core can be accomplished using various pathways described in the art (See. e.g., Kok et al. (2001). "A New Synthesis of Valienamine," J. Org. Chem. 66:7184-90). Compositions of the present invention can be synthesized by halogenation during the valienamine synthesis process.

One exemplary synthesis is shown in Process Scheme 1. It is understood by a person of ordinary skill in the art that the desired stereochemistry and constituents of the desired product can be obtained using analogous reagents and substitutions in the appropriate stage of the synthesis pathway.

Process Scheme 1:

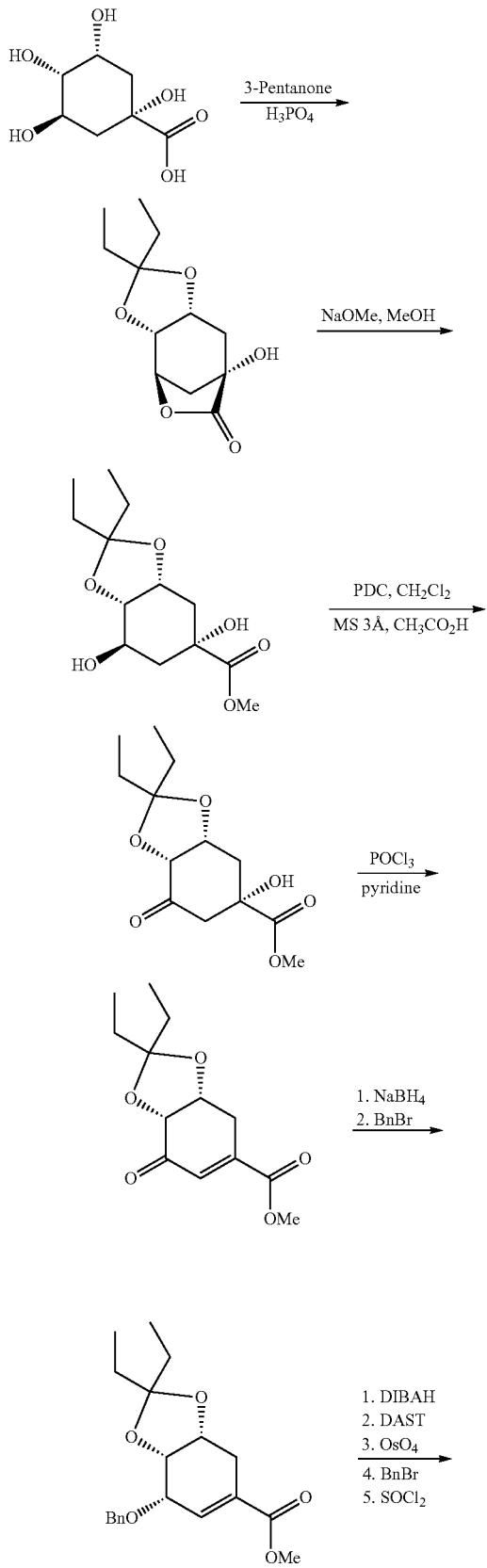

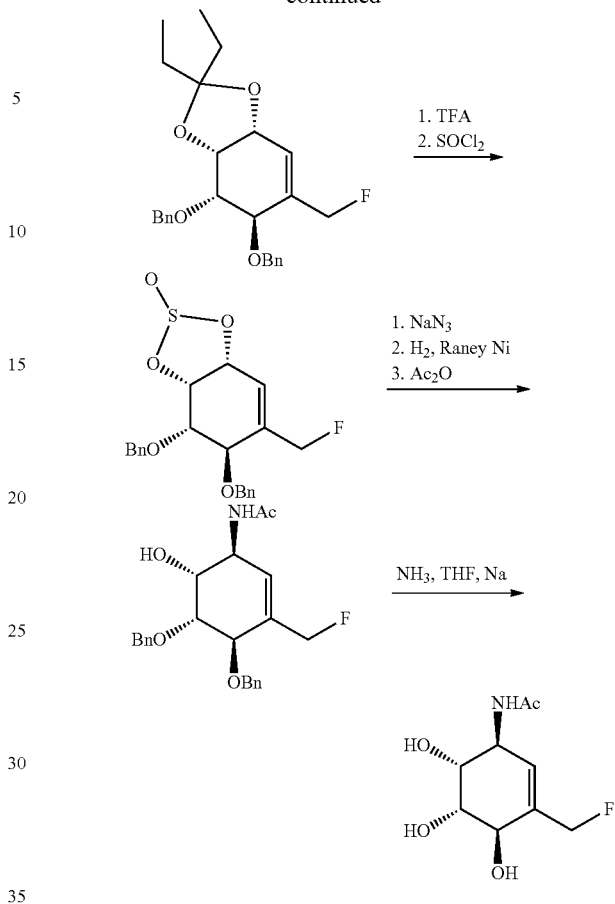

Salts, Solvates and Prodrugs

Compounds of the present invention include pharmaceutically acceptable salts, solvates and pro-drugs of the compounds disclosed herein. Pharmaceutically acceptable salts include salts derived from inorganic bases such as Li, Na, K, Ca, Mg, Fe, Cu, Zn, Mn; salts of organic bases such as N,N'-diacetylethylenediamine, glucamine, triethylamine, choline, hydroxide, dicyclohexylamine, metformin, benzylamine, trialkylamine, thiamine; chiral bases like alkylphenylamine, glycinol, phenyl glycinol, salts of natural amino acids such as glycine, alanine, valine, leucine, isoleucine, norleucine, tyrosine, cystine, cysteine, methionine, proline, hydroxy proline, histidine, ornithine, lysine, arginine, serine; non-natural amino acids such as D-isomers or substituted amino acids; guanidine, substituted guanidine wherein the substituents are selected from nitro, amino, alkyl, alkenyl, alkynyl, ammonium or substituted ammonium salts and aluminum salts. Salts may include acid addition salts where appropriate which are, hydrochlorides, sulphates, nitrates, phosphates, perchlorates, borates, hydrohalides, acetates, tartrates, maleates, citrates, succinates, palmoates, methanesulphonates, benzoates, salicylates, benzenesulfonates, ascorbates, glycerophosphates, ketoglutarates. In one embodiment, the pharmaceutically acceptable salt of the compounds disclosed herein is the hydrochloride salt.

"Solvate" denotes a physical association of a compound with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. "Hydrate" is a solvate wherein the solvent molecule is $H_2O$. Other non-limiting examples of suitable solvates include alcohols (e.g., ethanolates, methanolates, and the like).

Prodrugs are compounds which are converted in vivo to active forms (see, e.g., R. B. Silverman, 1992, "The Organic Chemistry of Drug Design and Drug Action", Academic Press, Chapter 8, incorporated herein by reference). Additionally, a discussion of prodrugs is provided in T. Higuchi and V. Stella, Pro-drugs as Novel Delivery Systems, Volume 14 of the A.C.S. Symposium Series, and in Bioreversible Carriers in Drug Design, Edward B. Roche, ed., American Pharmaceutical Association and Pergamon Press, 1987, both of which are incorporated herein by reference thereto. Prodrugs can be used to alter the biodistribution (e.g., to allow compounds which would not typically enter the reactive site of the protease) or the pharmacokinetics for a particular compound. For example, a carboxylic acid group, can be esterified, e.g., with a methyl group or an ethyl group to yield an ester. When the ester is administered to a subject, the ester is cleaved, enzymatically or non-enzymatically, reductively, oxidatively, or hydrolytically, to reveal the anionic group. An anionic group can be esterified with moieties (e.g., acyloxymethyl esters) which are cleaved to reveal an intermediate compound which subsequently decomposes to yield the active compound.

Examples of prodrugs and their uses are well known in the art (See, e.g., Berge et al. (1977) "Pharmaceutical Salts", *J. Pharm. Sci.* 68:1-19). The prodrugs can be prepared in situ during the final isolation and purification of the compounds, or by separately reacting the purified compound with a suitable derivatizing agent. For example hydroxy groups can be converted into esters via treatment with a carboxylic acid in the presence of a catalyst. Examples of cleavable alcohol prodrug moieties include substituted and unsubstituted, branched or unbranched lower alkyl ester moieties, (e.g., ethyl esters), lower alkenyl esters, di-lower alkyl-amino lower-alkyl esters (e.g., dimethylaminoethyl ester), acylamino lower alkyl esters, acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides.

All stereoisomers (for example, geometric isomers, optical isomers and the like) of the compounds disclosed herein (including those of the salts, solvates and prodrugs of these compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. Individual stereoisomers of these compounds may, for example, be substantially free of other isomers, or may be admixed, for example, as racemates or with all other, or other selected, stereoisomers. The chiral centers of the aforementioned compounds can have the S or R configuration as defined by the IUPAC 1974 Recommendations. The use of the terms "salt", "solvate" "prodrug" and the like, is intended to equally apply to the salt, solvate and prodrug of enantiomers, stereoisomers, rotamers, tautomers, racemates or prodrugs of the compounds of the present invention disclosed herein.

Formulations

The therapeutic agent(s) can be formulated to be suitable for any route of administration, including e.g., orally in the form of tablets or capsules or liquid, or in sterile aqueous solution for injection. When the therapeutic agent(s) is formulated for oral administration, tablets or capsules can be prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or another suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); or preservatives (e.g., methyl or propyl-p-hydroxybenzoates or sorbic acid). The liquid preparations may also contain buffer salts, flavoring, coloring or sweetening agents as appropriate. Preparations for oral administration may be suitably formulated to give controlled or sustained release of the therapeutic agent(s).

In certain embodiments of the present invention, the therapeutic agent(s) is administered in a dosage form that permits systemic uptake, such that the therapeutic agent(s) may cross the blood-brain barrier so as to exert effects on neuronal cells. For example, pharmaceutical formulations of the therapeutic agent(s) suitable for parenteral/injectable use generally include sterile aqueous solutions (where water soluble), or dispersions and sterile powders for the extemporaneous preparation of sterile injectable solutions or dispersion. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, polyethylene glycol, and the like), suitable mixtures thereof, or vegetable oils. The proper fluidity can be maintained, for example, by the use of a coating such as lecithin, by the maintenance of the required particle size in the case of dispersion and by the use of surfactants. Prevention of the action of microorganisms can be brought about by various antibacterial and antifungal agents, for example, parabens, chlorobutanol, phenol, benzyl alcohol, sorbic acid, and the like. In many cases, it will be reasonable to include isotonic agents, for example, sugars or sodium chloride. Prolonged absorption of the Injectable compositions can be brought about by the use in the compositions of agents delaying absorption, for example, aluminum monosterate or gelatin.

Sterile injectable solutions are prepared by incorporating the therapeutic agent(s) in the required amount in the appropriate solvent with various of the other ingredients enumerated above, as required, followed by filter or terminal sterilization. Generally, dispersions are prepared by incorporating the various sterilized active Ingredients into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

The formulation can contain an excipient. Pharmaceutically acceptable excipients which may be included in the formulation are buffers such as citrate buffer, phosphate buffer, acetate buffer, and bicarbonate buffer, amino acids, urea, alcohols, ascorbic acid, phospholipids; proteins, such as serum albumin, collagen, and gelatin; salts such as EDTA or EGTA, and sodium chloride; liposomes; polyvinylpyrrolidone; sugars, such as dextran, mannitol, sorbitol, and glycerol; propylene glycol and polyethylene glycol (e.g., PEG-4000, PEG-6000); glycerol; glycine or other amino acids; and lipids. Buffer systems for use with the formulations include citrate; acetate; bicarbonate; and phosphate buffers. Phosphate buffer is a preferred embodiment.

The formulation can also contain a non-ionic detergent. Preferred non-ionic detergents include Polysorbate 20, Polysorbate 80, Triton X-100, Triton X-114, Nonidet P-40, Octyl α-glucoside, Octyl β-glucoside, Brij 35, Pluronic, and Tween 20.

Routes of Administration

The therapeutic agent(s) may be administered orally or parenterally, including intravenously, subcutaneously, intra-arterially, intraperitoneally, ophthalmically, intramuscularly, buccally, rectally, vaginally, intraorbitally, intracerebrally, intradermally, intracranially, intraspinally, intraventricularly, intrathecally, intracisternally, intracapsularly, intrapulmonarily, intranasally, transmucosally, transdermally, or via inhalation. In one preferred embodiment, the therapeutic agent(s) is administered orally.

Administration of therapeutic agent(s) may be by periodic injections of a bolus of the formulation, or may be administered by intravenous or intraperitoneal administration from a reservoir which is external (e.g., an i.v. bag) or internal (e.g., a bioerodible implant). See, e.g., U.S. Pat. Nos. 4,407,957 and 5,798,113, each incorporated herein by reference. Intrapulmonary delivery methods and apparatus are described, for example, in U.S. Pat. Nos. 5,654,007, 5,780,014, and 5,814,807, each incorporated herein by reference. Other useful parenteral delivery systems include ethylene-vinyl acetate copolymer particles, osmotic pumps, implantable infusion systems, pump delivery, encapsulated cell delivery, liposomal delivery, needle-delivered injection, needle-less injection, nebulizer, aerosolizer, electroporation, and transdermal patch. Needle-less injector devices are described in U.S. Pat. Nos. 5,879,327; 5,520,639; 5,846,233 and 5,704,911, the specifications of which are herein incorporated by reference. Any of the formulations described above can be administered using these methods.

Subcutaneous injections have the advantages allowing self-administration, while also resulting in a prolonged plasma half-life as compared to Intravenous administration. Furthermore, a variety of devices designed for patient convenience, such as refillable injection pens and needle-less injection devices, may be used with the formulations of the present invention as discussed herein.

Dosage

A suitable pharmaceutical preparation is in a unit dosage form. In such form, the preparation is subdivided into suitably sized unit doses containing appropriate quantities of the active component, e.g., an effective amount to achieve the desired purpose. In certain embodiments, the therapeutic agent(s) is administered in one or more daily doses (e.g., once-a-day, twice-a-day, thrice-a-day). In certain embodiments, the therapeutic agent(s) is administered in Intermittently.

Exemplary dosing regimens are described in International patent application PCT/US08/61764 published as WO 2008/134628 on Jun. 11, 2008 and U.S. provisional patent application 61/108,192, filed on Oct. 24, 2008, both of which are incorporated by reference herein in their entirety. In one embodiment, the therapeutic agent(s) is administered in an intermittent dosing regimen that includes an initial "loading dose" given daily, followed by a period of non-daily Interval dosing.

The amount of effective therapeutic agent(s) for preventing or treating the referenced disorder can be determined on a case-by-case basis by those skilled in the art. The amount and frequency of administration of the therapeutic agent(s) will be regulated according to the judgment of the attending clinician (physician) considering such factors as age, condition and size of the patient as well as risk for developing disorder or severity of the symptoms of the referenced disorder being treated.

Combination Drug Therapy

The therapeutic agent(s) of the present invention can be administered in combination with at least one other therapeutic agent. Administration of the therapeutic agent(s) of the present invention with at least one other therapeutic agent is understood to encompass administration that is sequential or concurrent. In one embodiment, the therapeutic agents are administered in separate dosage forms. In another embodiment, two or more therapeutic agents are administered concurrently in the same dosage form.

In certain embodiments, the therapeutic agent(s) of the present invention are administered in combination with at least one other therapeutic agent which is an anti-dyskinesia Agent (e.g., Carbidopa, Levodopa), an anti-infective agent (e.g., Miglustat), an antineoplastic agent (e.g., Busulfan, Cyclophosphamide), a gastrointestinal agent (e.g., Methylprednisolone), a micronutrient (e.g., Calcitriol, Cholecalciferol, Ergocalciferols, Vitamin D), a vasoconstrictor agent (e.g., Calcitriol).

In certain embodiments, the therapeutic agent(s) of the present invention are administered in combination with allopregnanolone, a low-cholesterol diet, or cholesterol-lowering agents such as statins (e.g., Lipitor®); fibrates such as fenofibrate (Lipdil®); niacin; and/or binding resins such as cholestyramine (Questran®).

In one embodiment, the therapeutic agent(s) of the present invention is administered in combination with gene therapy. Gene therapy is contemplated both with replacement genes such as glucocerebrosidase or with inhibitory RNA (siRNA) for the SNCA gene. Gene therapy is described in more detail in U.S. Pat. No. 7,446,098, filed on Feb. 17, 2004.

In one embodiment, the therapeutic agent(s) of the present invention is administered in combination with at least one other therapeutic agent which is an anti-inflammatory agent (e.g., ibuprofen or other NSAID).

In one embodiment, the therapeutic agent(s) of the present invention is administered in combination with a substrate inhibitor for glucocerebrosidase, such as N-butyl-deoxynojimycin (Zavesca®; miglustat available from Actelion Pharmaceuticals, US, Inc., South San Francisco, Calif., US).

Combinations of the therapeutic agent(s) of the present invention with at least one other therapeutic agent which is a therapeutic agent for one or more other lysosomal enzymes are also contemplated. Table 2 is a non-limiting list of therapeutic agents for lysosomal enzymes.

TABLE 2

| LYSOSOMAL ENZYME | THERAPEUTIC AGENT |
|---|---|
| α-Glucosidase<br>GenBank Accession No.<br>Y00839<br>Acid β-Glucosidase (β-glucocerebrosidase)<br>GenBank Accession No.<br>J03059 | 1-deoxynojirimycin (DNJ)<br>a-homonojirimycin<br>castanospermine<br>isofagomine<br>C-benzyl isofagomine and derivatives<br>N-alkyl (C9-12)-DNJ<br>Glucoimidazole (and derivatives)<br>C-alkyl-IFG (and derivatives)<br>N-alkyl-β-valeinamines<br>Fluphenozine<br>calystegines $A_3$, $B_1$, $B_2$ and $C_1$ |
| α-Galactosidase A<br>GenBank Accession No.<br>NM000169 | 1-deoxygalactonojirimycin (DGJ)<br>α-allo-homonojirimycin<br>α-galacto-homonojirimycin<br>β-1-C-butyl-deoxynojirimycin<br>calystegines $A_2$ and $B_2$<br>N-methyl caiystegines $A_2$ and $B_2$ |
| Acid β-Galactosidase<br>GenBank Accession No.<br>M34423 | 4-epi-isofagomine<br>1-deoxygalactonojirimyion |
| Galactocerebrosidase<br>(Acid β-Galactosidase)<br>GenBank Accession No.<br>D25283 | 4-epi-isofagomine<br>1-deoxygalactonojirimycin |
| Acid α-Mannosidase<br>GenBank Accession No.<br>U68567 | 1-deoxymannojirimycin<br>Swainsonine<br>Mannostatin A |
| Acid β-Mannosidase<br>GenBank Accession No.<br>U60337 | 2-hydroxy-isofagomine |
| Acid α-L-fucosidase<br>GenBank Accession No.<br>NM_000147 | 1-deoxyfuconojirimycin<br>β-homofuconojirimycin<br>2,5-imino-1,2,5-trideoxy-L-glucitol<br>2,5-deoxy-2,5-imino-D-fucitol<br>2,5-imino-12,5-trideoxy-D-altritol |
| α-N-Acetylglucosaminidase<br>GenBank Accession No.<br>U40846 | 1,2-dideoxy-2-N-acetamido-nojirimycin |
| α-N-Acetylgalactosaminidase<br>GenBank Accession No.<br>M62783 | 1,2-dideoxy-2-N-acetamido-galactonojirimycin |
| β-Hexosaminidase A<br>GenBank Accession No.<br>NM_000520 | 2-N-acetylamino-isofagomine<br>1,2-dideoxy-2-acetamido-nojirimycin<br>Nagstatin |
| β-Hexosaminidase B<br>GenBank Accession No.<br>NM_000521 | 2-N-acetamido-isofagomine<br>1,2-dideoxy-2-acetamido-nojirimycin<br>Nagstatin |
| α-L-Iduronidase<br>GenBank Accession No.<br>NM_000203 | 1-deoxyiduronojirimycin<br>2-carboxy-3,4,5-trideoxypiperidine |
| β-Glucuronidase<br>GenBank Accession No.<br>NM_000181 | 6-carboxy-isofagomine<br>2-carboxy-3,4,5-trideoxypiperidine |
| Sialidase<br>GenBank Accession No.<br>U84246 | 2,6-dideoxy-2,6, imino-sialic acid<br>Siastatin B |
| Iduronate sulfatase<br>GenBank Accession No.<br>AF_011889 | 2,5-anhydromannitol-6-sulphate |
| Acid sphingomyelinase<br>GenBank Accession No.<br>M59916 | desipramine, phosphatidylinositol-4,5-diphosphate |

In certain embodiments, the therapeutic agent(s) of the present invention are administered in combination with at least one therapeutic agent which is an anti-dyskinesia Agent (e.g., Carbidopa, Levodopa), an anti-infective agent (e.g., Cyclosporine, Miglustat, Pyrimethamine), an antineoplastic agent (e.g., Alemtuzumab, Azathioprine, Busulfan, Clofarabine, Cyclophosphamide, Melphalan, Methotrexate, Rituximab), an antirheumatic agent (e.g., Rituximab) a gastrointestinal agent (e.g., Methylprednisolone), a micronutrient (e.g., Calcitriol, Cholecalciferol, Ergocalciferols, Folic Acid, Vitamin D), a reproductive control agent (e.g., Methotrexate), a respiratory system agent (e.g., Tetrahydrozoline), vasoconstrictor agent (e.g., Calcitriol, Tetrahydrozoline).

In certain embodiments, the therapeutic agent(s) of the present invention are administered in combination with at least one therapeutic agent which is a therapeutic agent for β-hexosaminidase A and/or a therapeutic agent for acid β-galactosidase. In certain embodiments, the therapeutic agent(s) of the present invention are administered in combination with at least one therapeutic agent which is an anti-Infective agent (e.g., Miglustat), an antineoplastic agent (e.g., Alemtuzumab, Busulfan, Cyclophosphamide), a gastrointestinal agent (e.g., Methylprednisolone).

The therapeutic agent(s) of the present invention can be administered in combination with at least one other therapeutic agent which includes but is not limited to, RNAi, dopamine replacement (e.g., levodopa (L-DOPA)), dopamine replacement stabilizer (e.g., carbidopa, and entacapone), anticholinergic (e.g., trihexyphenidyl, benzatropine mesylate (Cogentin®), trihexyphenidyl HCL (Artane®), and procyclidine), catechol-O-methyltransferase (COMT) Inhibitor (e.g., entacapone (Comtan®) and tolcapone (Tasmar®)), dopamine receptor agonist (e.g., bromocriptine (Parlodel®), pramipexole (Mirapex®), ropinirole (Requip®)), pergolide (Permax), and APOKYN™ injection (apomorphine hydrochloride), monoamine oxidase (MAO) inhibitor (i.e., MAO-A and/or MAO-B inhibitors, e.g., selegiline (Deprenyl, Eldepryl®, Carbex®), selegiline HCl orally disintegrating tablet (Zelapar®), and rasagiline (Azilect®)), peripheral decarboxylase inhibitor, amantadine (Symmetrel®), and rivastigmine tartrate (Exelon®).

Also contemplated are combinations of the therapeutic agent(s) of the present invention with more than one other therapeutic agent. Exemplary combinations of other therapeutic agents include, but are not limited to, carbidopa/levodopa (Sinemet® or Parcopa®), carbidopa, levodopa and entacapone (Stalevo®), levodopa with a dopamine receptor agonist such as bromocriptine (Parlodel®), pramipexole (Mirapex®), ropinirole (Requip®)), pergolide (Permax), or APOKYN™ injection (apomorphine hydrochloride).

In one embodiment, the therapeutic agent(s) of the present invention is administered in combination with vaccine therapy, such as a vaccine comprising alpha-synuclein and an adjuvant (Pilcher et al., Lancet Neurol. 2005; 4(8):458-9).

In one embodiment, the therapeutic agent(s) of the present invention is administered in combination with at least one other therapeutic agent that may be protective such as dextromethorphan (Li et al., FASEB J. 2005; April; 19(6): 489-96); genistein (Wang et al., Neuroreport. 2005; February 28; 16(3):267-70), or minocycline (Blum et al., Neurobiol Dis. 2004; December; 17(3):359-66).

In one embodiment, the therapeutic agent(s) of the present invention is administered in combination with at least one other therapeutic agent which is therapeutic agent for alpha-synuclein (e.g., Hsp70).

Patients having Parkinson's disease experience tremor, rigidity, bradykinesia, and postural imbalance. Patients having Lewy Body Dementia experience strong psychotic symptoms (visual hallucinations) in addition to mental decline such as memory loss and an inability to carry out simple tasks. Observable improvements in symptoms, or a delay of onset of certain symptoms in patients at risk of developing a disorder, or a delay in progression of the disorder will be evidence of a favorable response to the therapies provided herein.

In addition, measurable surrogate markers also may be useful for evaluating response to therapy. For instance, some investigators have reported detecting higher levels of alpha-synuclein or oligomeric forms of alpha-synuclein have been detected in the plasma of patients with Parkinson's disease (Lee et al., *J Neural Transm.* 2006; 113(10):1435-9; El-Agnaf et al., *FASEB J.* 2006; 20(3):419-25), while some have reported decreased plasma alpha-synuclein in Parkinson's patients compared with normal controls (Li et al., Exp Neurol. 2007; 204(2):583-8).

In certain embodiments, the therapeutic agent(s) of the present invention is administered in combination with at least one other therapeutic agent which is an alcohol deterrent (e.g., Acamprosate), a narcotic analgesic (e.g., Remifentanil), an anti-dyskinesia agent (e.g, Amantadine, Apomorphine, Benserazide, Bromocriptine, Cabergoline, Carbidopa, Dexetimide, Droxidopa, Entacapone, Levodopa, Lisuride, Memantine, Piribedil, Pramipexol, Ropinirole, Selegiline, Sinemet), an anti-infective agent (e.g. Amantadine, Amoxicillin, Clardthromycin, Ethanol, Interferons, Minocycline, PS-K), an anti-obesity agent (e.g., Phenylpropanolamine, Topiramate), an anticonvulsant (e.g., Etiracetam, Topiramate), an antiemetic (e.g., Trimethobenzamide), an antihypertensive agent (e.g., Trandolapril), an antineoplastic agent (e.g., Cabergoline, PS-K), central nervous system depressant (e.g., Aripiprazole, Benzocaine, Clozapine, Cocaine, Dexmedetomidine, Diphenhydramine, isoflurane, Lithium, Lithium Carbonate, Metylperon, Morphine, Propofol, Quetiapine, Raclopride, Remifentanil, Sodium Oxybate), a central nervous system stimulant (e.g., Caffeine citrate, Modafinil, Nicotine polacrilex), a coagulant (e.g., Arginine Vasopressin, Deamino Arginine Vasopressin, Vasopressins), a dermatologic agent (e.g., Loratedine, Promethazine), a gastrointestinal agent (e.g., Diphenhydramine, Domperidone, Omeprazole, Trimethobenzamide), a hypnotic and/or sedative (e.g., Remifentanil), a micronutrient (e.g., Alpha-Tocopherol, Coenzyme Q10, Ergocalciferols, Hydroxocobalamin, Iron, Tocopherol acetate, Tocopherols, Vitamin B 12, Vitamin D, Vitamin E), a neuroprotective agent (e.g., Eliprodil, Modafinil, Rasagiline, Rivastigmine, Topiramate), a nootropic agent (e.g., Donepezil, Etiracetam), a psychotropic drug (e.g., Aripiprazole, Citalopram, Clozapine, Duloxetine, Lithium, Lithium Carbonate, Metylperon, Nortriptyline, Paroxetine, Quetiapine, Raciopride, Venkafaxine), a respiratory system agent (e.g., Dextromethorphan, Guaifenesin, Ipratropium, Naphazoline, Oxymetazoline, Phenylephrine, Phenylpropanolamine), a vasoconstrictor agent (e.g., Naphazoline, Oxymetazoline, Phenylephrine, Phenylpropanolamine).

In one preferred embodiment, the aforementioned other therapeutic agents are administered when the disorder is Parkinson's disease.

In certain embodiments, the therapeutic agent(s) of the present invention is administered in combination with at least one other therapeutic agent which is a nicotinic alpha-7 agonist (e.g., MEM 3454 or MEM 83905 both of which are available from Memory Pharmaceuticals). In certain embodiments, the therapeutic agent(s) of the present invention is administered in combination with at least one other therapeutic agent which is R3487 and/or R4996 (both of which are available from Roche). Also contemplated are combinations of the therapeutic agent(s) of the present invention with more than one other therapeutic agents. Exemplary combinations of other therapeutic agents include, but are not limited to, R3487/MEM 3454 and R4996/MEM 63908.

In certain embodiments, the therapeutic agent(s) of the present invention is administered in combination with at least one cholinesterase inhibitor (e.g., donepezil (brand name Aricept), galantamine (brand name Razadyne), and rivastigmine (branded as Exelon and Exelon Patch).

In certain embodiments, the therapeutic agent(s) of the present invention is administered in combination with at least one noncompetitive NMDA receptor antagonist (e.g., memantine (brand names Akatinol, Axura, EblxelAbixa, Memox and Namenda)).

In certain embodiments, the therapeutic agent(s) of the present invention is administered in combination with at least one other therapeutic agent which is a non-narcotic analgesic (e.g., Celecoxib, Resveratrol, Rofecoxib, TNFR-Fc fusion protein), an anti-dyskinesia agent (e.g., Dexetimide, Gabapentin, Levodopa, Memantine), an anti-infective agent (e.g., Acetylcysteine, Acyclovir, Benzoates, Deoxyglucose, Doxycycline, Interferon Alfa-2a, Interferon-alpha, Interferons, Moxifloxacin, PS-K, Quinacrine, Rifampin, Salicylic Acid, Valacyclovir), an anti-inflammatory agent (e.g., Aspirin, Celecoxib, Curcumin, Ibuprofen, Indomethacin, Naproxen, Resveratrol, Rofecoxib, TNFR-Fc fusion protein), an anti-obesity agent (e.g., Phenylpropanolamine), an anticonvulsant agent (e.g., Gabapentin, Homotaurine, Lamotrigine), an antiemetic (e.g., Olanzapine), an antihypertensive agent (e.g., Trandolapril), an antilipemic agent (e.g., Atorvastatin, Choline, Clofibric Acid, Pravastatin, Simvastatin), an antineoplastic agent (e.g., Bryostatin 1, Carmustine, Cyclophosphamide, Interferon Alfa-2a, Leuprolide, Medroxyprogesterone 17-Acetate, Methyltestosterone, PK 11195, Prednisone, PS-K, Resveratrol, 2,3-dihydro-1H-imidazo(1,2-b)pyrazole), an antirheumatic agent (e.g., Aspirin, Celecoxib, Curcumin, Ibuprofen, Indomethacin, Naproxen, Resveratrol, Rofecoxib, TNFR-Fc fusion protein), a central nervous system depressant (e.g., Aripiprazole, Benzocaine, Cocaine, Gabapentin, Haloperidol, Haloperidol decanoate, Lithium, Lithium Carbonate, Lorazepam, Midazolam, Olanzapine, Perphenazine, Propofol, Quetiapine, Risperidone, Sodium Oxybate, Trazodone, Valproic Acid, Zolpidem), a central nervous system stimulant (e.g., Caffeine citrate, Modafinil, Nicotine polacrilex), a channel blocker (e.g., Gabapentin, Lamotrigine), a coagulant (e.g., Antiplasmin, Vitamin K), a dermatologic agent (e.g., Mineral Oil, Salicylic Acid), a gastrointestinal agent (e.g., Choline, Haloperidol, Lorazepam, Olanzapine, Omeprazole, TNFR-Fc fusion protein), a hypnotic and/or sedative agent (e.g., Zolpidem), a hypoglycemic agent (e.g., Insulin, Asp (B28)-, Rosiglitazone), a micronutrient (e.g., Alpha-Tocopherol, Ascorbic Acid, Coenzyme Q10, Copper, Folic Acid, Hydroxocobalamin, Inositol, iron, Niacin, Niacinamide, Nicotinic Acids, Pyridoxine, Selenium, Thioctic Acid, Tocopherol acetate, Tocopherols, Vitamin B 12, Vitamin B 8, Vitamin E, Vitamin K), a neuroprotective agent (e.g., Huperzine A, Modafinil, Nefiracetam, Rasagiline, Rivastigmine, (3-aminopropyl)(n-butyl)phosphinic acid), a nootropic agent (e.g., Donepezil, Nefiracetam), a platelet aggregation inhibitor (e.g., Resveratrol), a psychotropic drug (e.g., Aripiprazole, Bupropion, Citalopram, Duloxetine, Gabapentin, Haloperidol, Haloperidol decanoate, Lithium, Lithium Carbonate, Lorazepam, Midazolam, Nefiracetam, Olanzapine, Paroxetine, Perphenazine, Quetiapine, Risperidone, Sertraline, Trazodone, Tryptophan, Valproic Acid, Venlafaxine), a reproductive control agent (e.g., Estradiol 17 beta-cypionate, Estradiol 3-benzoate, Estradiol valerate, indomethacin, Leuprolide, Medroxyprogesterone, Medroxyprogesterone 17-Acetate, Mifepristone), a respiratory system agent (e.g., Acetylcysteine, Dextromethorphan, Gualfenesin, Naphazoline, Oxymetazoline, Phenylephrine, Phenylpropanolamine), or a vasoconstrictor agent (e.g., Naphazoline, Oxymetazoline, Phenylephrine, Phenylpropanolamine).

What is claimed:

1. A compound of Formula III:

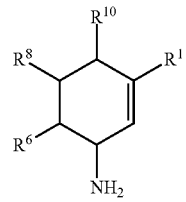

wherein:
R$^1$ is C(R$^2$)(R$^3$)(R$^4$);
R$^2$ is selected from the group consisting of hydrogen, —OH or halogen;
R$^3$ is selected from the group consisting of hydrogen, —OH, halogen or —CH$_3$;
R$^4$ is selected from the group consisting of hydrogen, halogen, —CH$_3$, phenyl, fluorophenyl, methylphenyl or cyclohexylmethyl;
R$^3$ and R$^4$ may join with the carbon to which they are attached to form a cycloalkyl ring, which may be optionally substituted with one or more halogen atoms;
R$^6$ is —OH;
R$^8$ is selected from the group consisting of —OH or halogen; and
R$^{10}$ is selected from the group consisting of —OH or halogen,
provided that that at least one of R$^2$, R$^3$, R$^4$, R$^8$ or R$^{10}$ comprises a halogen.

2. A compound selected from the group consisting of the following:

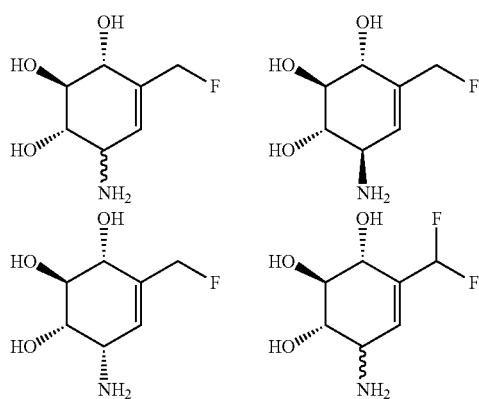

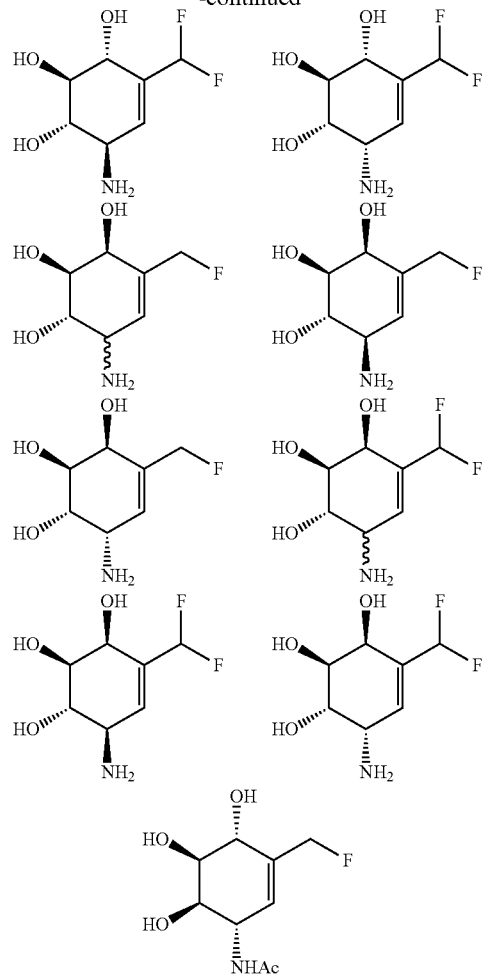

or a pharmaceutically acceptable salt, thereof.

3. A kit comprising:
a container having an effective amount of a compound of claim 2, or a pharmaceutically acceptable salt, or solvate thereof, or any combination of two or more thereof; and
instructions for using the same to treat a degenerative disorder of the central nervous system or a lysosomal storage disorder.

4. A pharmaceutical composition comprising the compound of claim 1 and at least one pharmaceutically acceptable carrier.

5. A pharmaceutical composition comprising the compound of claim 2 and at least one pharmaceutically acceptable carrier.

* * * * *

UNITED STATES PATENT AND TRADEMARK OFFICE
CERTIFICATE OF CORRECTION

PATENT NO.         : 11,358,926 B2
APPLICATION NO.    : 16/608592
DATED              : June 14, 2022
INVENTOR(S)        : Robert Boyd It is certified that error appears in the above-identified patent and that said Letters Patent is hereby corrected as shown below:

In the Claims

- Claim 2, Column 26, Line 40, after "salt," and before "thereof", insert --or solvate--.

Signed and Sealed this
Second Day of August, 2022

Katherine Kelly Vidal
*Director of the United States Patent and Trademark Office*